(12) United States Patent
Zhang (10) Patent No.: US 10,597,352 B1
(45) Date of Patent: Mar. 24, 2020

(54) STABLE ALKYL BENZIDINE COMPOSITION AND METHODS OF MAKING AND USING SAME

(71) Applicant: OneStep Technologies Inc., Burnaby (CA)

(72) Inventor: Hao Zhang, Vancouver (CA)

(73) Assignee: OneStep Technologies Inc., Burnaby (CA)

( * ) Notice: Subject to any disclaimer, the term of this patent is extended or adjusted under 35 U.S.C. 154(b) by 0 days.

(21) Appl. No.: 16/453,878

(22) Filed: Jun. 26, 2019

Related U.S. Application Data (60) Provisional application No. 62/809,631, filed on Feb. 23, 2019.

(51) Int. Cl.
*C07C 209/90* (2006.01)
*C07C 211/50* (2006.01)

(52) U.S. Cl.
CPC .......... *C07C 209/90* (2013.01); *C07C 211/50* (2013.01); *C07C 2601/16* (2017.05)

(58) Field of Classification Search
CPC .. C07C 209/90; C07C 2601/16; C07C 211/50
See application file for complete search history.

(56) References Cited

U.S. PATENT DOCUMENTS

| | | | |
|---|---|---|---|
| 4,888,413 A | 12/1989 | Domb | |
| 5,206,150 A | 4/1993 | Tai | |
| 5,804,404 A | 9/1998 | Heras et al. | |
| 5,972,713 A | 10/1999 | Kuzuhara et al. | |
| 9,228,986 B2 | 1/2016 | Xiao et al. | |
| 9,714,939 B1 * | 7/2017 | Zhang | G01N 33/52 |
| 2007/0072305 A1 * | 3/2007 | Mitsumoto | G01N 31/224 |
| | | | 436/166 |

FOREIGN PATENT DOCUMENTS

JP 06022794 A * 2/1994

OTHER PUBLICATIONS

BC Renal (Chemical & Chlorine Sampling of Dialysis Water, Dec. 2017, recovered from http://www.bcrenalagency.ca/resource-gallery/Documents/Chemical%20and%20Chlorine%20Sampling% 20of% 20Dialysis%20Water.pdf. (Year: 2017).*
I. Jaunakais, "Advances in Chlorine Testing". Water Quality Products. Jul. 2011, 18-19.
Kasper et al., "Synthesis of Poly(Propylene Fumarate)". Nat. Protoc. Author manuscript; available in PMC2011 Apr. 2014.
Marfurt et al., "Stabilization of tetramethylbenzidine (TMB) reaction product at the electron microscopic level by ammonium molybdate". Journal of Neuroscience Methods, 25 (1988) 215-223.

* cited by examiner

*Primary Examiner* — Paul A Zucker
(74) *Attorney, Agent, or Firm* — Oyen Wiggs Green & Mutala LLP (57) ABSTRACT

Stable formulations of alkyl benzidine compounds and methods of making and using same. To prepare a stable formulation, a short chain diol having fewer than six carbon atoms and an alkyl benzidine compound are combined together in solution at low pH and the solution is heated with moderate heat in the range of about 50° C. to 80° C. The stable formulation may contain dimers and/or trimers of the short chain diol. The stable formulation can be used to detect total chlorine in aqueous solution, to detect total chlorine in dialysis water, or as a colorimetric substrate in enzyme-linked immunosorbent assays.

18 Claims, 12 Drawing Sheets

STABLE ALKYL BENZIDINE COMPOSITION AND METHODS OF MAKING AND USING SAME

REFERENCE TO RELATED APPLICATIONS

This application claims the benefit of U.S. provisional patent application No. 62/809,631 filed 23 Feb. 2019, which is incorporated by reference herein in its entirety.

TECHNICAL FIELD

Some embodiments of the present invention pertain to stable formulations of alkyl benzidine compounds, including dialkyl benzidine compounds and tetraalkyl benzidine compounds. Some embodiments pertain to methods of making such formulations. Some embodiments pertain to methods of using such formulations.

BACKGROUND

Alkyl benzidine compounds, including dialkyl benzidine compounds and tetraalkyl benzidine compounds such as 3,3',5,5'-tetramethylbenzidine (TMB) have many uses. For example, such compounds can be used as colorimetric reagents to measure the amount of free chlorine present in an aqueous solution, for example as described in U.S. Pat. No. 5,972,713, which is incorporated by reference herein in its entirety, or as colorimetric substrates for use in enzyme-linked immunosorbent assays (ELISA), in which the colorimetric substrate is, for example, oxidized by an enzyme such as horseradish peroxidase to result in the generation of a visible colour change.

Chlorine is frequently used as a disinfecting agent to control microorganisms that may be present in domestic water supplies, including drinking water and water used for swimming or bathing. A disinfecting level of chlorine would include a level of approximately 1 part per million (ppm) chlorine. As an example, a recommended chlorine concentration is about 1 ppm in swimming pools and is about 3 ppm in hot tubs.

Various sources of chlorine can be used for water disinfection, including chlorine gas ($Cl_2$), calcium hypochlorite ($Ca(OCl)_2$), or sodium hypochlorite (NaOCl). All of these sources form hypochlorous acid (HClO) in water. Hypochlorous acid is the principal effective disinfecting agent when chlorine is used as the disinfecting agent.

Reactions can occur that affect the performance of hypochlorous acid as a disinfecting agent. First, chlorine can react with hydroxide ion ($OH^-$), which is readily available in aqueous solutions having an alkaline pH to form a hypochlorite ion ($OCl^-$). A hypochlorite ion is only about two-thirds as effective as a disinfecting agent as compared with hypochlorous acid. The sum of hypochlorous acid and hypochlorite ions present in a solution is referred to as the free chlorine.

Second, chlorine can react with ammonia ($NH_3$) and organic nitrogen compounds including proteins and amino acids to form chloramines, as monochloramine ($NH_2Cl$), dichloramine ($NHCl_2$) and nitrogen trichloride ($NCl_3$). Chloramines are less effective as a disinfecting agent. The sum of the chloramine species present in a solution is referred to as the combined chlorine. Total chlorine is the sum of both the free chlorine and the combined chlorine present in a solution.

In order to ensure that a sufficient amount of chlorine is present in a water sample to permit the safe consumption or use of the water, testing is frequently conducted. Many existing tests to measure the amount of chlorine present in water use N,N-diethyl-p-phenylenediamine (DPD) or o-tolidine. However, concerns have arisen regarding the toxicity of these compounds, meaning that alternative assays are needed.

Because chlorine is toxic and excess of chlorine can cause health problems, chlorine concentration is often monitored and controlled. For example, the chlorine concentration in most disinfected drinking water is about 0.2-1 ppm, and the chlorine concentration in dialysis water is even lower and may be e.g. less than 0.1 ppm. If there is too much chlorine present in dialysis water, there can be extremely severe effects on the patient. As an example, in one instance a patient died when a chlorine test of dialysis water with diethyl-p-phenylene diamine (DPD) yielded a false negative result due to bleaching of the DPD.

3,3',5,5'-tetramethylbenzidine (TMB) is an exemplary alkyl benzidine compound that is a colorimetric substrate that can be used in various assays, including chlorine testing, enzyme-linked immunosorbent assays (ELISA), and immunohistochemistry. TMB can act as a hydrogen donor for the reduction of hydrogen peroxide to water by peroxidases such as horseradish peroxidase. This causes the solution to change to a blue colour. The reaction can be stopped by the addition of acid or another stop reagent, which turns the TMB a yellow colour.

Many alkyl benzidine compounds, including dialkyl benzidine compounds and tetraalkyl benzidine compounds such as TMB, are not soluble in water. Traditional methods of dissolving alkyl benzidine compounds such as TMB have used solvents such as dimethyl sulfoxide (DMSO) or dimethylformamide (DMF). Even when dissolved in such solvents, solutions of TMB developed to date do not exhibit good storage stability. Thus, when TMB is to be used in an assay, the solution of the alkyl benzidine compound, e.g. TMB, to be used must be freshly prepared. This is inconvenient to those carrying out the assay.

A stable formulation of TMB has been previously disclosed by the inventor in U.S. Pat. No. 9,714,939, which is incorporated by reference herein in its entirety. That formulation still incorporates a significant proportion (10% v/v) of DMSO as a solvent, and has the TMB being initially dissolved into the DMSO solvent.

There is a general desire for improved formulations of alkyl benzidine compounds, including dialkyl benzidine compounds and tetraalkyl benzidine compounds.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In some aspects, a method for preparing a stable formulation of an alkyl benzidine compound is provided. A short chain diol and an alkyl benzidine compound are combined in a solution having a low pH and the solution is heated with moderate heat. In some aspects, the alkyl benzidine compound is a dialkyl benzidine compound or a tetraalkyl benzidine compound. In some aspects the short chain diol is propylene glycol.

In some aspects the low pH is provided by adding an acid to the solution. In some aspects, the pH is in the range of about 2.0 to about 6.0. In some aspects, the solution is heated at a temperature in the range of about 50° C. to about 80° C. In some aspects, the solution is heated for a treatment period of between about 10 minutes and about 10 hours.

In some aspects, a stable formulation prepared according to the foregoing methods is used to detect total chlorine in an aqueous solution such as pool or hot tub water, drinking water, or dialysis water. In some aspects, a stable formulation prepared according to the foregoing methods is used as a colorimetric substrate in enzyme-linked immunosorbent assays or immunohistochemistry.

In some aspects, a stable formulation of an alkyl benzidine compound includes an alkyl benzidine compound in solution with dimers and/or trimers of a short chain diol. In some aspects, the short chain diol is propylene glycol.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

As used herein, "low pH" means a pH less than 7. In some embodiments, a low pH is a pH in the range of about 2 to about 6, including e.g. 2.5, 3.0, 3.5, 4.0, 4.5, 5.0 or 5.5 or any subrange defined between any of those values. In some embodiments, a low pH is a pH in the range of about 2.0 to about 3.0, including any value therebetween e.g. 2.1, 2.2, 2.3, 2.4, 2.5, 2.6, 2.7, 2.8 or 2.9.

As used herein, the term "long-term storage stability" means that a solution of a given compound is stable (i.e. that the given compound does not precipitate or undergo undesired chemical reactions) for a period of at least 18 months at room temperature (i.e. at 22° C.). It will be appreciated by those skilled in the art that storage stability may differ depending on the temperature at which a compound is stored. For example, if a compound is maintained in a refrigerated state, e.g. at a temperature of around 4° C., the compound would be stable for a longer period of time, e.g. 4 years. Likewise, if the compound is stored at an elevated temperature, e.g. at a temperature of around 37° C., the compound would be stable for a shorter period of time, e.g. around 2 months. While longer storage stabilities can be achieved by keeping a solution at a cooler temperature, it may be commercially undesirable to do so, for example due to increased shipping and storage costs incurred to maintain a solution in a refrigerated state.

Exemplary alkyl benzidine compounds that can be used in some embodiments, including dialkyl benzidine compounds and tetraalkyl benzidine compounds are described, for example, in US patent application publication No. 2007/0072305 to Mitsumoto, which is incorporated by reference herein in its entirety. For example, such compounds may have the general formula (I):

(I)

wherein $R_1$ and $R_2$ each independently represent an alkyl group having from 1 to 6 carbon atoms, $R_3$ and $R_4$ each independently represent an alkyl group having 1 to 6 carbon atoms or a hydrogen atom, $R_5$ and $R_6$ each independently represent an alkyl group having 1 to 8 carbon atoms or a hydrogen atom, and $R_7$ and $R_8$ each independently represent a hydrogen atom, a sulfoalkyl group having 1 to 8 carbon atoms which may have one or more hydroxyl groups, or a carboxyalkyl group having 1 to 8 carbon atoms which may have one or more hydroxyl groups, and $R_7$ and $R_8$ are not simultaneously H.

Non-limiting examples of dialkyl benzidine compounds having the general formula (I) include N,N'-bis(2-sulfoethyl)-3,3'-dimethylbenzidine; N,N'-bis(3-sulfopropyl)-3,3'-dimethylbenzidine; N,N'-bis(2-hydroxy-2-sulfoethyl)-3,3'-dimethylbenzidine; N,N'-bis(2-hydroxy-3-sulfopropyl)-3,3'-dimethylbenzidine; N,N'-bis(4-sulfobutyl)-3,3'-dimethylbenzidine; N,N'-bis(3-sulfopropyl)-N,N'-diethyl-3,3'-dimethylbenzidine; N,N'-bis(2,4-disulfobenzyl)-3,3'-dimethylbenzidine; and alkali metal salts thereof.

Non-limiting examples of tetraalkyl benzidine compounds having the general formula (I) include N-(2-sulfoethyl)-3,3',5,5'-tetramethylbenzidine; N-(3-sulfopropyl)-3,3',5,5'-tetramethylbenzidine; N-(4-sulfobutyl)-3,3',5,5'-tetramethylbenzidine; N-(2-hydroxy-2-sulfoethyl)-3,3',5,5'-tetramethylbenzidine; N-(2-hydroxy-3-sulfopropyl)-3,3',5,5'-tetramethylbenzidine; N-(2,4-disulfobenzyl)-3,3',5,5'-tetramethylbenzidine; N,N'-bis(2-sulfoethyl)-3,3',5,5'-tetramethylbenzidine; N,N'-bis(3-sulfopropyl)-3,3',5,5'-tetramethylbenzidine; N,N'-bis(4-sulfobutyl)-3,3',5,5'-tetramethylbenzidine; N,N'-bis(2-hydroxy-2-sulfoethyl)-3,3',5,5'-tetramethylbenzidine; N,N'-bis(2-hydroxy-3- sulfopropyl)-3,3',5,5'-tetramethylbenzidine; N,N'-bis(2,4-disulfobenzyl)-3,3',5,5'-tetramethylbenzidine; and alkali metal salts thereof.

The inventor has now discovered that a stable formulation of an alkyl benzidine compound, including a dialkyl benzidine compound or a tetraalkyl benzidine compound such as 3,3',5,5'-tetramethylbenzidine (TMB) can be prepared by reacting the compound at a low pH with a short chain diol such as propylene glycol. As used herein, the term "short chain" means a compound having fewer than 6 carbon atoms, i.e. between 1 and 5 carbon atoms. In some embodiments, beta-cyclodextrin is also added. The resulting formulation can be used in any assay in which the alkyl benzidine compound is typically used, for example for detecting free and total chlorine in aqueous solution, for conducting immunological assays, for example as a substrate for horseradish peroxidase, for use in immunohistochemistry, or the like.

In some embodiments, the low pH for the reaction is obtained by providing the alkyl benzidine compound and the propylene glycol in an acidic solution. In some embodiments, to achieve an acidic solution, an acid is added to a solution containing the alkyl benzidine compound and/or the propylene glycol. In some embodiments, the acid is an organic acid. In some embodiments, the acid is a short chain organic acid, including a short chain unsaturated carboxylic acid such as fumaric acid ($C_4H_4O_4$) or a short chain saturated carboxylic acid such as citric acid ($C_6H_8O_7$), malic acid ($C_4H_6O_5$), lactic acid ($C_3H_6O_3$), acetic acid ($C_2H_4O_2$), or the like. In some embodiments, the acid is an inorganic acid, such as hydrochloric acid (HCl), sulfuric acid ($H_2SO_4$), carbonic acid ($H_2CO_3$), phosphoric acid ($H_3PO_4$) or the like. In some embodiments, the low pH is provided by adding two or more different acids. In some embodiments, the low pH is provided by adding two or more of the acids listed above.

In one aspect, the formulation results in an alkyl benzidine preparation that has long-term storage stability at room temperature, and which does not require the use of DMSO, DMF or other like substances as a solvent. In one specific example embodiment, the formulation results in a preparation of the exemplary tetraalkyl benzidine TMB that is stable for a period of at least 18 months at room temperature. In some embodiments, the formulation results in preparation of an alkyl benzidine compound that is stable for a period of at least two years at room temperature. In contrast, currently available preparations of alkyl benzidine compounds such as TMB are prepared in DMSO or DMF solvent due to the low solubility of the compound, and are not stable at room temperature.

One aspect of the present invention relates to the formulation of a solution containing an alkyl benzidine, including a dialkyl benzidine or a tetraalkyl benzidine such as TMB to be used in colorimetric assays, e.g. in chlorine detection, immunohistochemistry, or ELISA. The resulting solution has a high alkyl benzidine concentration, with good solubility and stability. The inventor observed one such solution to be stable in this concentrated form at room temperature over a period of 24 months.

In some embodiments, the preparation comprises a chromogenic compound and a short chain diol in a solution having a low pH. In some embodiments, the preparation comprises a chromogenic compound, a short chain diol, and an acid. In some embodiments, the chromogenic compound is an alkyl benzidine. In some embodiments, the chromogenic compound is a dialkyl benzidine. In some embodiments, the chromogenic compound is a tetraalkyl benzidine.

In some embodiments, to produce the stable formulation of the chromogenic compound, the chromogenic compound and the short chain diol are combined in a solution having a low pH and heated at moderate heat (e.g. in the range of about 50° C. to about 80° C. including any value therebetween, e.g. 55, 60, 65, 70 or 75° C.) with stirring for a treatment period. In some embodiments, to produce the stable formulation of the chromogenic compound, the chromogenic compound, short chain diol and acid are combined in solution and heated at moderate heat (e.g. in the range of about 50° C. to about 80° C. including any value therebetween, e.g. 55, 60, 65, 70 or 75° C.) with stirring for a treatment period.

In some embodiments, the chromogenic compound is present at a concentration in the range of between 0.1 mM and 100 mM, including any value therebetween, e.g. 0.2, 0.5, 1, 2, 5, 10, 15, 20, 25, 30, 40, 50, 60, 70, 80 or 90 mM. In some embodiments, the chromogenic compound is an alkyl benzidine compound. In some embodiments, the chromogenic compound is a dialkyl benzidine compound or a tetraalkyl benzidine compound. In some embodiments, the chromogenic compound is tetramethyl benzidine (TMB).

In some embodiments in which an acid is used to provide the low pH, the acid is present at a concentration in the range of between 0.1 mM and 50 mM, including any value therebetween, e.g. 0.2, 0.5, 1, 2, 5, 10, 15, 20, 25, 30, 35, 40, or 45 mM. In some embodiments, higher concentrations could be used. In some embodiments, the acid is an organic acid. In some embodiments, the organic acid is a short chain organic acid. In some embodiments, the organic acid is a short chain saturated organic acid. In some embodiments, the organic acid is a short chain unsaturated organic acid. In some embodiments, the organic acid is citric acid, fumaric acid, malic acid, lactic acid, acetic acid, or the like. In other embodiments, the acid is an inorganic acid, such as hydrochloric acid, sulfuric acid, carbonic acid, phosphoric acid or the like. In some embodiments, the acid is a combination of different acids. In some embodiments, the acid is a combination of any two or more of the foregoing organic and/or inorganic acids.

In some embodiments, the solvent in which the formulation is prepared is a short chain diol. In some embodiments, the solvent in which the preparation is prepared is propylene glycol.

In one non-limiting example embodiment, the solution contains the alkyl benzidine at a concentration in the range of about 10 mM to about 60 mM and an acid at a concentration in the range of about 10 mM to about 20 mM in propylene glycol as a solvent.

In some embodiments, once the chromogenic compound and the acid (if used) have been combined into the solvent, the mixture is heated with moderate heat, e.g. in the range of between about 50° C. to about 80° C., including any value therebetween, e.g. 55, 60, 65, 70 or 75° C. In some embodiments, the mixture is heated with stirring. In some embodiments, the mixture is heated with stirring for a treatment period of between about 10 minutes and about 10 hours, including any period of time therebetween, e.g. 20 minutes, 30 minutes, 40 minutes, 50 minutes, 60 minutes, 1.5 hours, 2 hours, 3 hours, 4 hours, 5 hours, 6 hours, 7 hours, 8 hours or 9 hours.

In some embodiments, the reaction conditions during the treatment period facilitate the formation of propylene glycol dimers. In some embodiments, the propylene glycol dimers stabilize the chromogenic compound, e.g. alkyl benzidine compound, e.g. dialkyl benzidine or tetraalkyl benzidine compound, e.g. TMB. In some embodiments, the reaction conditions facilitate the formation of propylene glycol trimers. In some embodiments, the propylene glycol trimers stabilize the chromogenic compound, e.g. alkyl benzidine compound, e.g. dialkyl benzidine or tetraalkyl benzidine compound, e.g. TMB. In some embodiments, a stable solution of an alkyl benzidine and propylene glycol dimers and/or trimers is provided.

Without being bound by theory, it is believed that the chromogenic compound, e.g. alkyl benzidine compound, e.g. dialkyl benzidine or tetraalkyl benzidine compound, e.g. TMB, and the propylene glycol react under acidic conditions to form larger molecules, including e.g. propylene glycol dimers and/or trimers, and/or chromogenic compound-propylene glycol polymers, at the moderate heating conditions applied.

In some embodiments, the chromogenic compound reacts with the acid to form a polymer. E.g. in one specific example embodiment, after adding fumaric acid in propylene glycol solvent and exposing to moderate heat, TMB may react with the fumaric acid to form a TMB-fumaric acid polymer. Subsequent to the reaction, the solution changes from colourless to a yellow color.

Without being bound by theory, it is believed that the acid promotes chemical reactions to form propylene glycol dimers and/or trimers, through the generation of $H^+$ in solution to trigger the polymerization reactions. Additionally, the acid is believed to promote solubility of the chromogenic compound (e.g. alkyl benzidine compound, e.g. dialkyl benzidine or tetraalkyl benzidine compound), propylene glycol dimers and/or trimers and/or chromogenic compound-propylene glycol polymers.

In some embodiments, the reaction products formed via this reaction process include propylene glycol dimers having the formula (1) (2-(2-hydroxypropyloxy)-1-propanol):

(1)

$C_6H_{15}O_3$
Molecular weight: 135

In some embodiments, a propylene glycol trimer having the formula (2) below (tripropylene glycol) is included in the reaction products formed by the process described above:

(2)

$C_9H_{20}O_4$
Molecular weight: 192

In contrast, control solutions in which DMSO was used as the solvent were found not to yield propylene dimers or trimers, and TMB dissolved in such solutions was not stable.

In some embodiments, it is believed the propylene glycol reacts with the alkyl benzidine compound to stabilize the alkyl benzidine compound. In one example embodiment, the propylene glycol reacts with the dialkyl benzidine compound or with the tetraalkyl benzidine compound to stabilize the dialkyl benzidine compound or the tetraalkyl benzidine compound. In one example embodiment, the reaction conditions yield a tetraalkyl benzindine compound complexed with two propylene glycol trimers, e.g. tetramethyl benzidine complexed with two propylene glycol trimers having the structure (3) shown below in embodiments in which the alkyl benzidine compound is TMB:

(3)

$C_{34}H_{60}O_8N_2$
Molecular weight: 624

In some embodiments, the chromogenic compound is further encased with beta-cyclodextrin (BCD) to enhance the stability of the chromogenic compound during the long term storage. In some embodiments, the alkyl benzidine compound is encased with BCD to enhance the stability of the alkyl benzidine compound during long term storage. In some embodiments, the dialkyl benzidine compound is encased with BCD to enhance the stability of the dialkyl benzidine compound during long term storage. In some embodiments, the tetraalkyl benzidine compound is encased with BCD to enhance the stability of the tetraalkyl benzidine compound during long term storage.

In some embodiments, the chromogenic compound formulation is stable for a period of at least 18 months at room temperature. In some embodiments, the chromogenic compound formulation is stable for a period of at least two years at room temperature.

In some embodiments, the stable chromogenic compound formulation is used in chlorine detection. In some embodiments, the chromogenic compound is TMB and the TMB formulation has a high TMB concentration, with good solubility and stability. The TMB in the TMB formulation is reactive to chlorine and the reaction product of chlorine with the TMB allows chlorine detection by visual comparison. The colour of the reaction product of chlorine and TMB is dependent on the pH of the solution. For example, at a pH level between 4 and 6, the reaction product has a blue color.

In some embodiments, the acid present in the stable chromogenic compound formulation also serves to reduce the pH of the resulting solution to be assayed, so that the chromogenic compound will absorb light having a desired wavelength. In some embodiments, the acid present in a stable TMB formulation also serves to reduce the pH of the resulting solution to be assayed, so that the TMB will absorb light having a wavelength of approximately 450 nm, and so that the resulting solution will have a blue colour by reason of the presence of the TMB and chlorine.

In some embodiments, the stabilized alkyl benzidine formulation is used to detect chlorine in dialysis water or other aqueous solutions intended for use in dialysis. For example, the British Columbia Provincial Health Services Authority advises that the maximum level of chlorine exposure allowed for dialysis patients is 0.1 ppm and therefore the chlorine concentration in dialysis water needs to be less than 0.1 ppm. The stabilized alkyl benzidine formulation can be used to test for total chlorine concentration in dialysis water.

In some embodiments the stabilized alkyl benzidine formulation is formulated so that reaction of the alkyl benzidine with chlorine present in aqueous solution will yield a blue colour change of the aqueous solution. In some embodiments, the solution of the stabilized alkyl benzidine at a concentration of between 10 mM to 60 mM, including any value therebetween e.g. 15, 20, 25, 30, 35, 40, 45, 50, or 55 mM, is formulated at a pH in the range of about 2 to about 6, including 2.5, 3.0, 3.5, 4.0, 4.5, 5.0 or 5.5. About 10 µL to about 100 µL, including any volume therebetween, e.g. 20, 30, 40, 50, 60, 70, 80 or 90 µL is added to approximately 4 mL to 10 mL of dialysis water, including any volume therebetween or therearound, including e.g. 1, 2, 4, 5, 6, 7, 8, 9, 11, 12, 15 or 20 mL of dialysis water, to yield a visible colour change. In one specific example embodiment, 30 mM TMB was used in a solution with 15 mM citric acid having a pH in the range of 2.0-3.0 to achieve a visible change to yield a blue colour upon addition to a sample of dialysis water if the level of chlorine present in a solution is above a level that is suitable for conducting dialysis.

In some embodiments, the stabilized alkyl benzidine formulation is a solution of TMB, and the concentration of TMB is in the range of 10 mM to 60 mM and 50 µl of the TMB formulation is added to 25 mL of dialysis water sample. The colour of the dialysis water sample will change from colourless to a blue colour if the total chlorine concentration in the sample is more than 0.1 ppm. The colour of the dialysis water sample will remain colourless if the total chlorine concentration in the sample if less than 0.1 ppm. Thus, the assay allows for a rapid visual determination of whether or not there is an unacceptably high level of chlorine present in the dialysis water.

In some embodiments, the stabilized alkyl benzidine formulation is used for conducting immunological assays, for example as a substrate for horseradish peroxidase, or for use in immunohistochemistry. In some such embodiments, the stabilized alkyl benzidine formulation is TMB. The TMB in the stabilized TMB formulation acts as a hydrogen donor for the reduction of hydrogen peroxide to water by horseradish peroxidase. This causes the solution to change to a blue colour. The reaction can be stopped by the addition of acid or another stop reagent, which turns the TMB a yellow colour.

EXAMPLES

Embodiments of the present invention are further described with reference to the following examples, which are intended to be illustrative not limiting in nature.

Example 1.0—Preparation and Characterization of Stable TMB Formulation

To prepare a final volume of 100 mL of a stable TMB formulation, 0.15 g fumaric acid was mixed with 99 mL propylene glycol with constant stirring for 20 minutes. 0.5 g TMB was added into the solution with constant stirring for 20 minutes at 60° C. 0.3 g BCD was added into the solution with constant stirring for 1 hour.

A mass spectrometer (Agilent 6495C Triple Quadrupole LC/MS) was used to identify and characterize components of the stable TMB formulation.

The TMB formulation is believed to contain the following compounds having the structures (1), (2) and (3) based on mass spectrometry analysis:

(1)

$C_6H_{15}O_3$
Molecular weight: 135

(2)

$C_9H_{20}O_4$
Molecular weight: 192

(3)

$C_{34}H_{60}O_8N_2$
Molecular weight: 624

Example 2.0—Preparation and Characterization of Stable TMB Formulations

The TMB formulations were prepared by first mixing solvent with an organic acid with constant stirring for 20 minutes. TMB was then added to the solution with constant stirring for 20 minutes at 60° C. For Preparations 4C, 4D and 4F, beta-cyclodextrin (BCD) was added with constant stirring for 1 hour. The reagents used to make the TMB preparation are listed in Table 1 below.

TABLE 1

Reagents Used to Make TMB Formulations

| | Solution 3C | Solution 3D | Solution 4C | Solution 4D | Solution 3F | Solution 4F |
|---|---|---|---|---|---|---|
| Solvent | Propylene glycol | DMSO | Propylene glycol | DMSO | Propylene glycol | Propylene glycol |

TABLE 1-continued

Reagents Used to Make TMB Formulations

| | Solution 3C | Solution 3D | Solution 4C | Solution 4D | Solution 3F | Solution 4F |
|---|---|---|---|---|---|---|
| TMB | 20 mM | 20 mM | 20 mM | 20 mM | 20 mM | 20 mM |
| Citric Acid | 10 mM | 10 mM | 10 mM | 10 mM | | |
| Fumaric acid | | | | | 10 mM | 10 mM |
| BCD | | | 4 mM | 4 mM | | 4 mM |

Figure 1A:
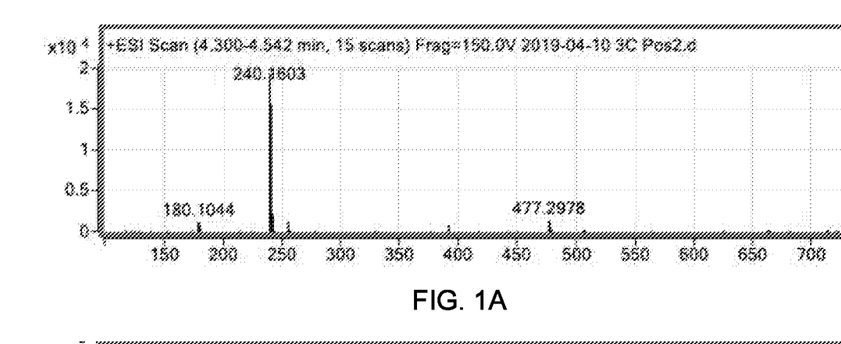
FIGS. 1A-1G show mass spectrometry results for an example solution of a stabilized TMB formulation according to one example embodiment.
Figure 1B:
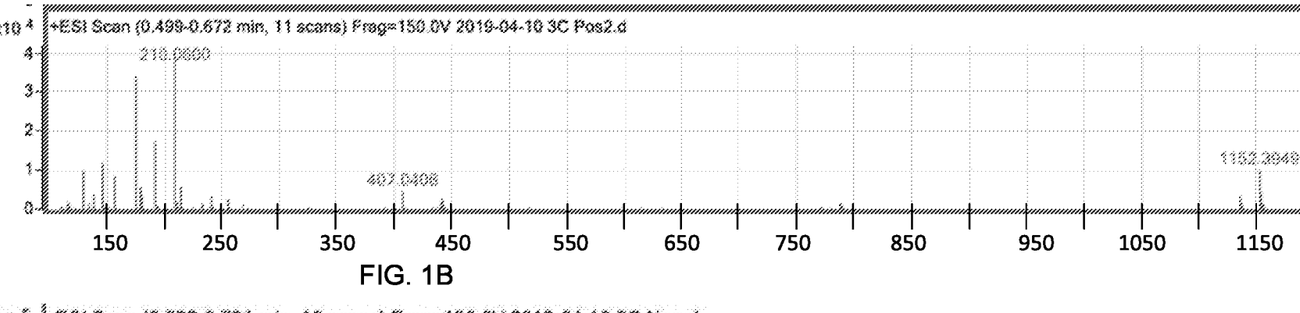
Figure 1C:
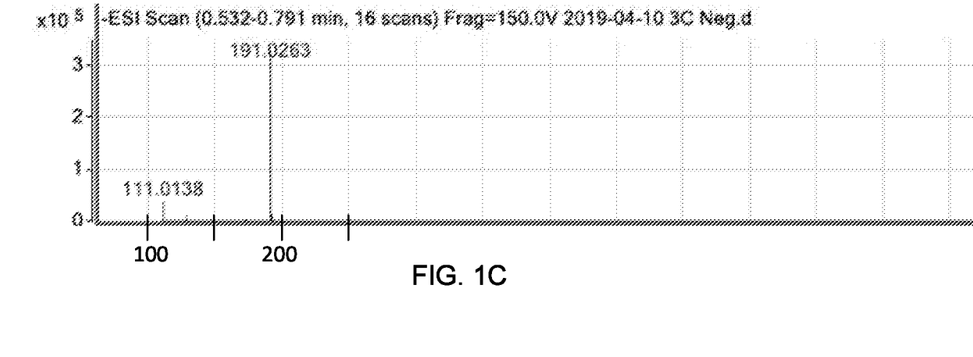
Figure 1D:
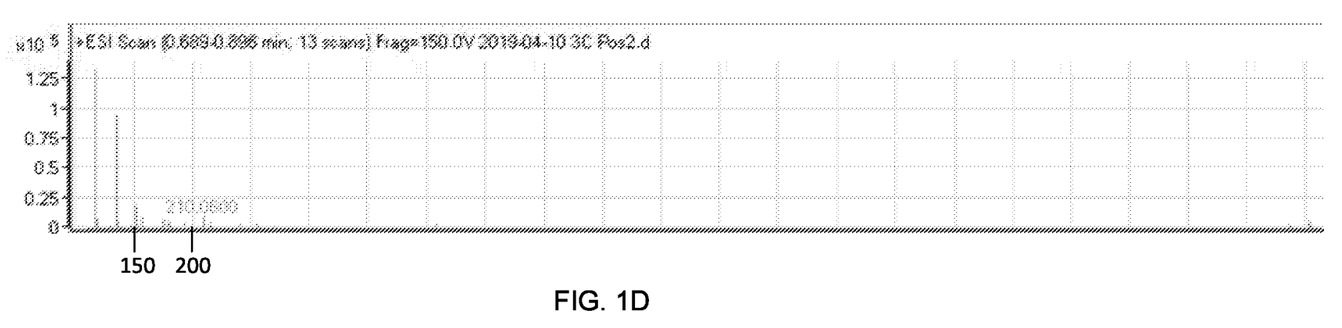
Figure 1E:
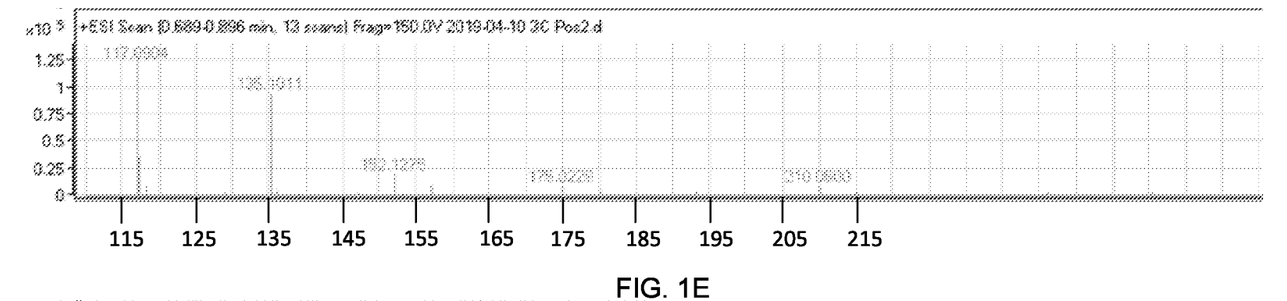
Figure 1F:
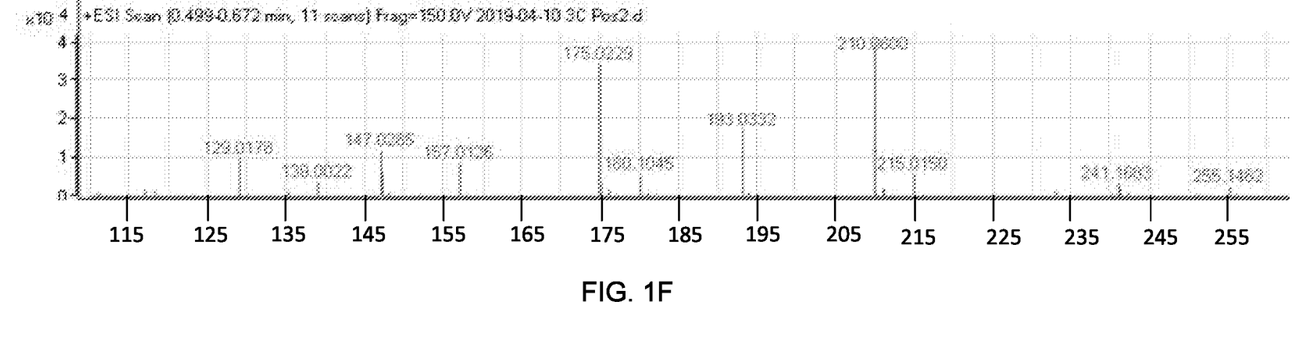
Figure 1G:
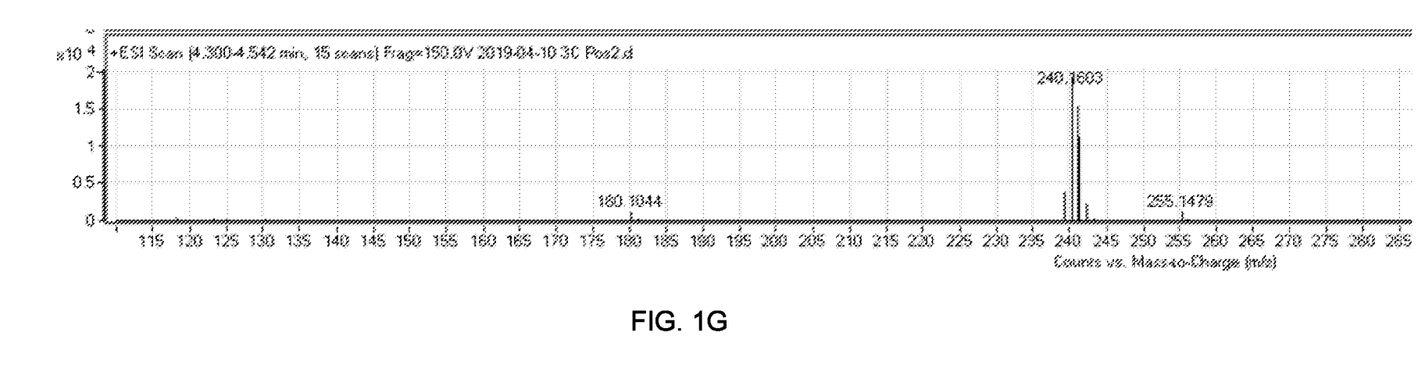
Figure 2A:
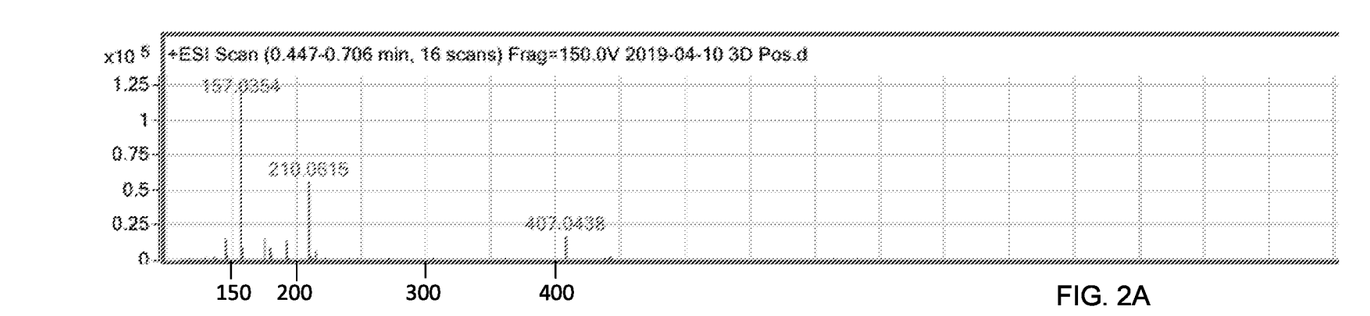
FIGS. 2A, 2B and 2C show mass spectrometry results for a control solution of TMB in the conventional solvent DMSO.
Figure 2B:
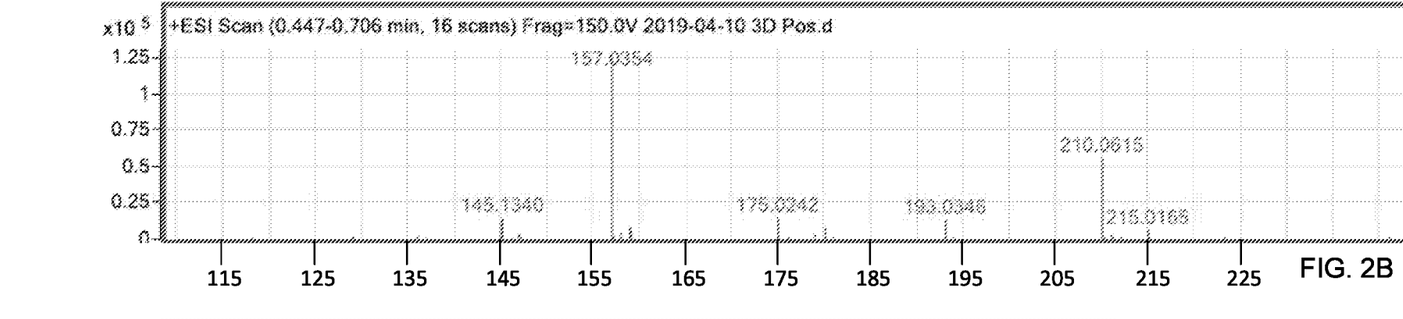
Figure 2C:
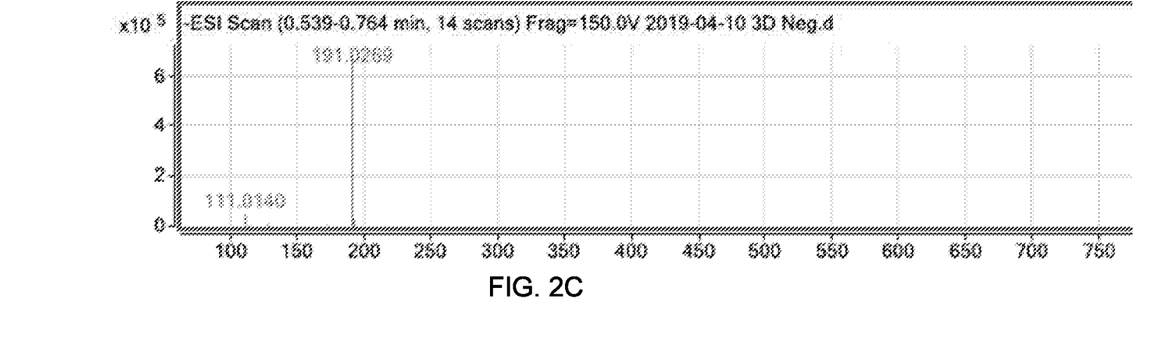
Figure 3A:
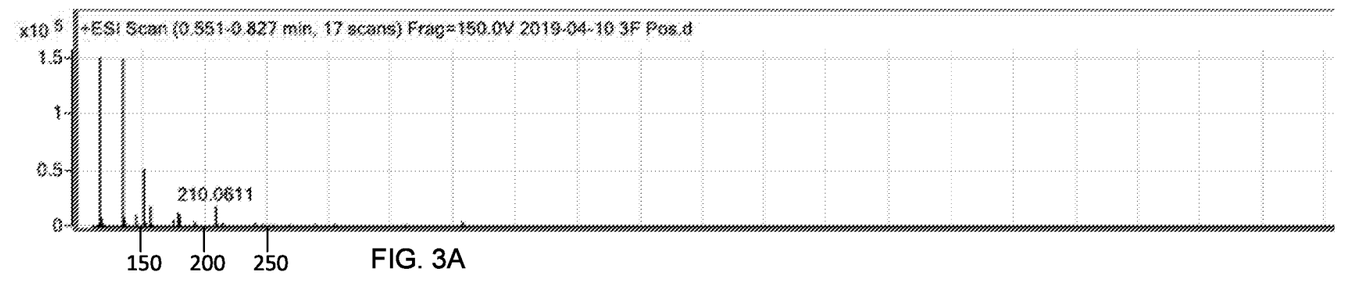
FIGS. 3A, 3B and 3C show mass spectrometry results for a solution of a stabilized TMB formulation according to one example embodiment.
Figure 3B:
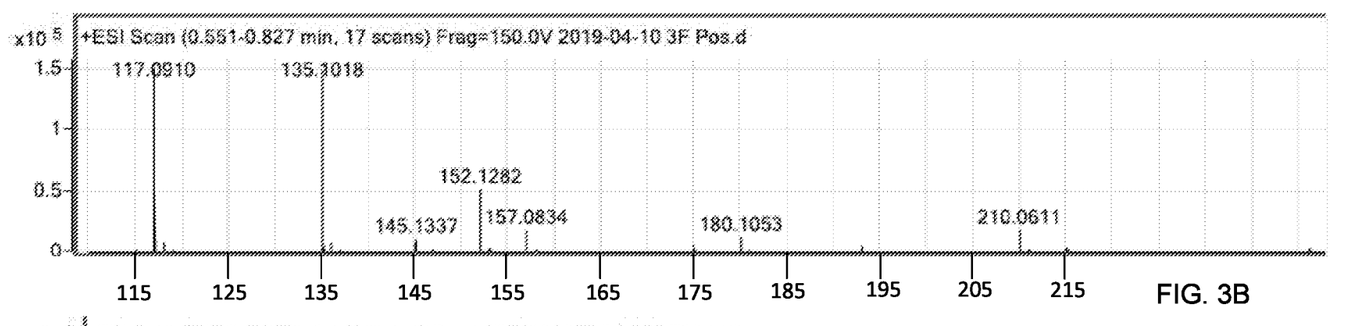
Figure 3C:
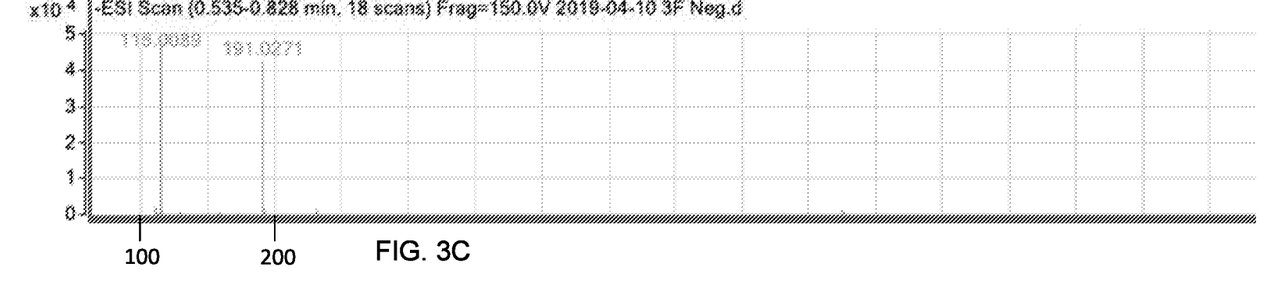
Figure 4A:
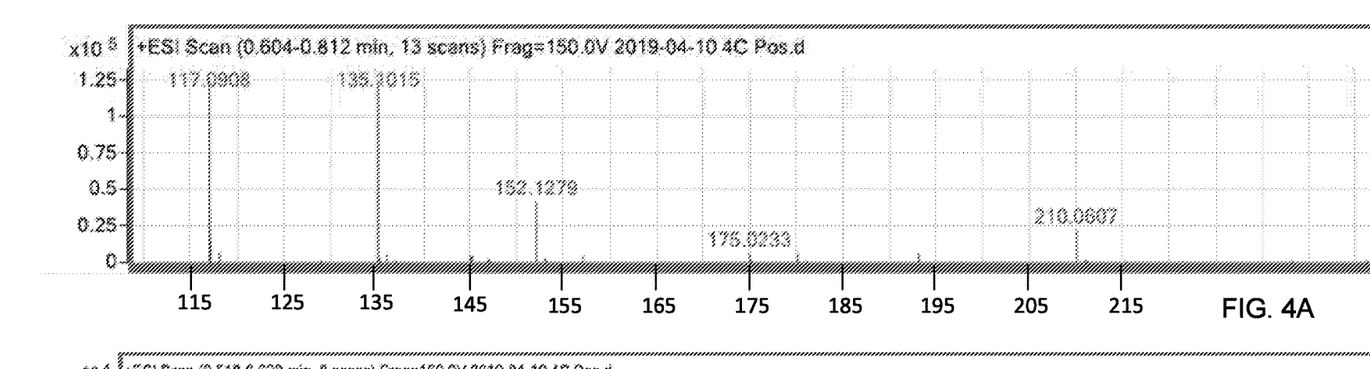
FIGS. 4A-4E show mass spectrometry results for a solution of a stabilized TMB formulation according to one example embodiment.
Figures 4B, 4C:
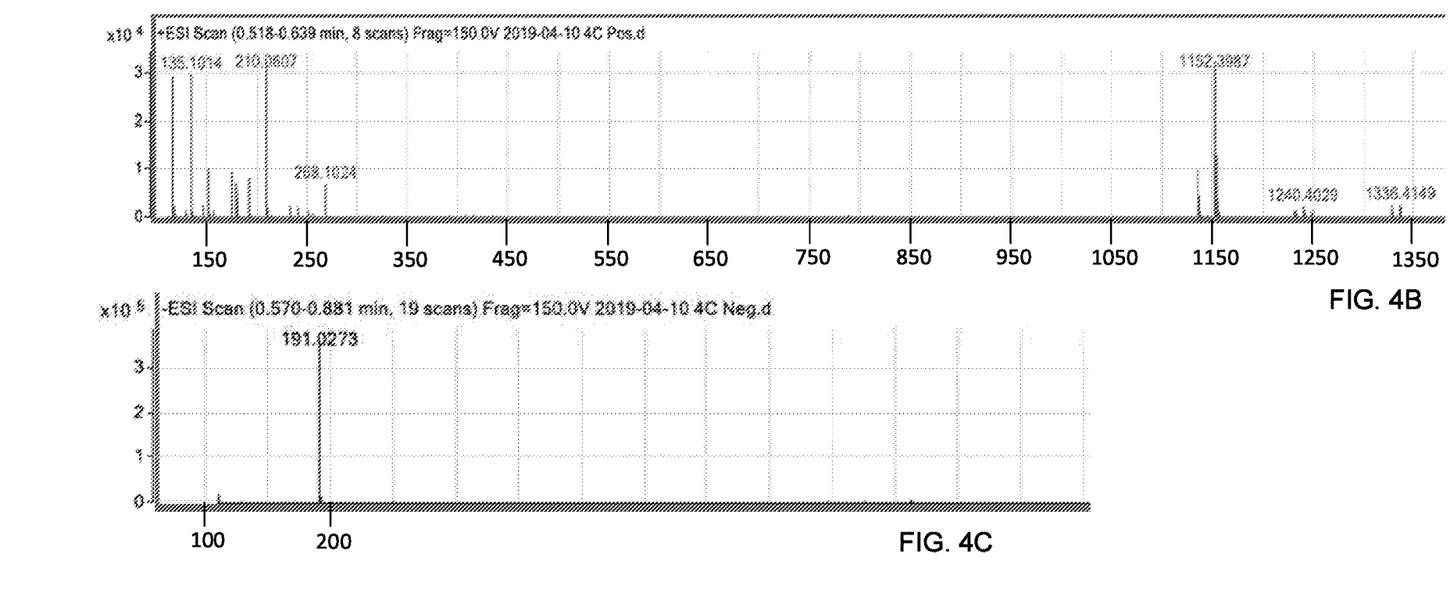
Figure 4D:
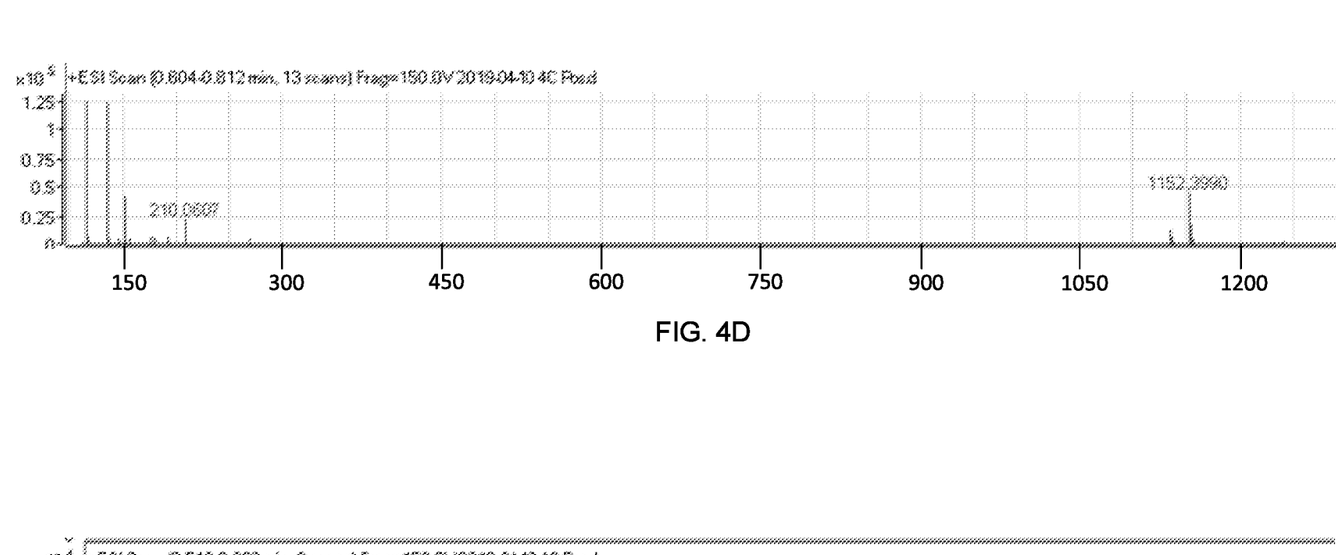
Figure 4E:
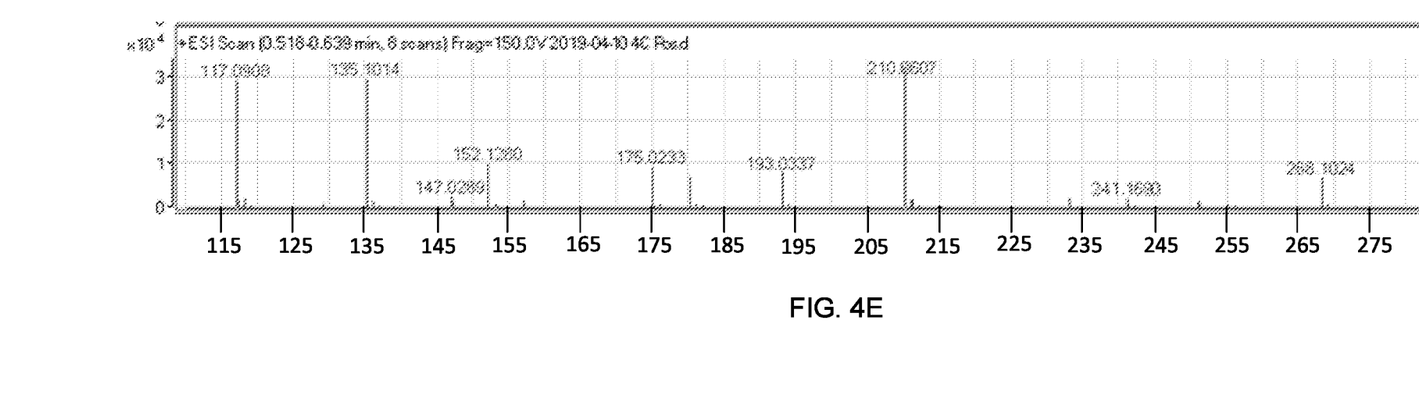
Figure 5A:
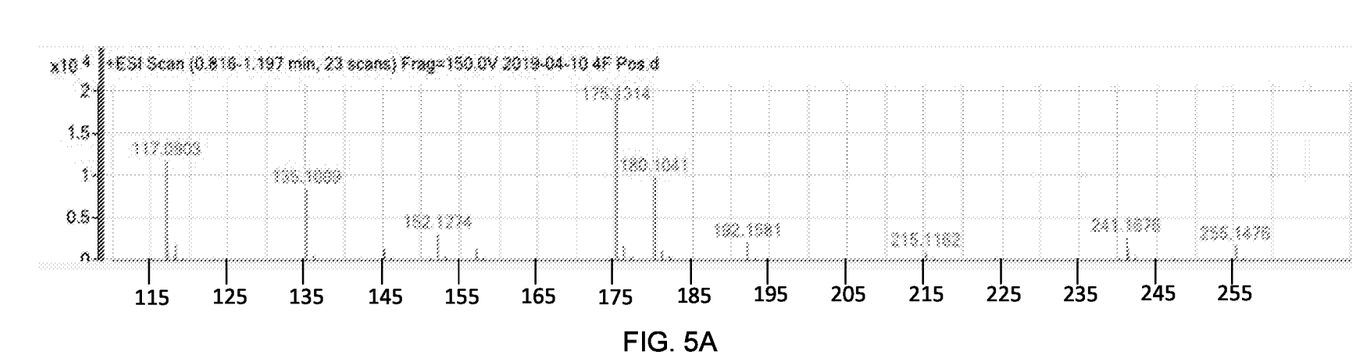
FIGS. 5A-5G show mass spectrometry results for a solution of a stabilized TMB formulation according to one example embodiment.
Figure 5B:
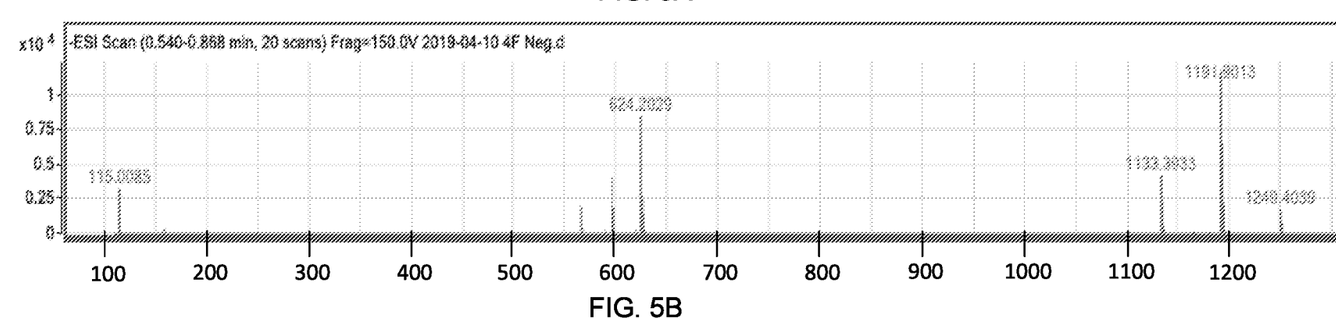
Figure 5C:
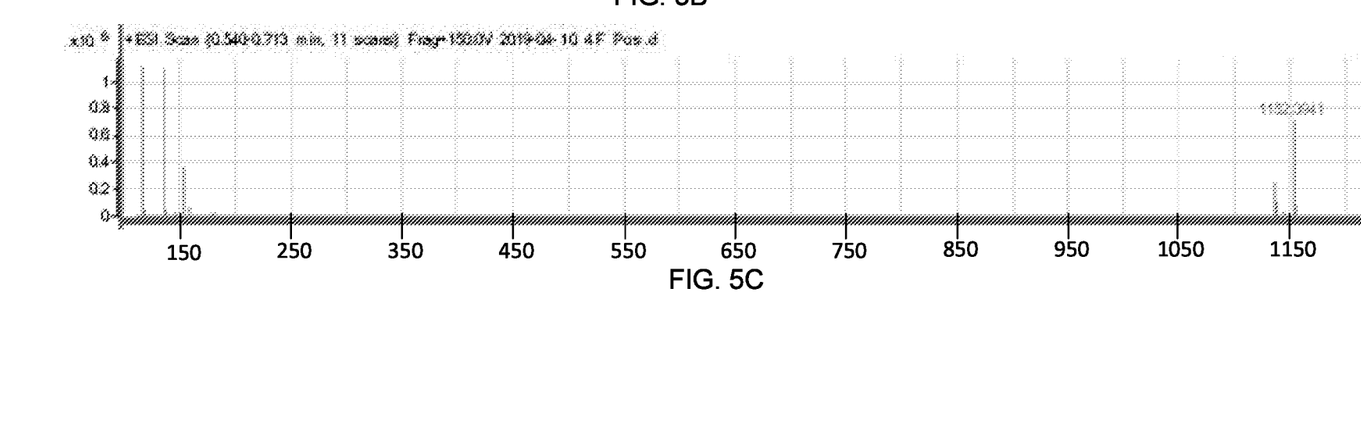
Figure 5D:
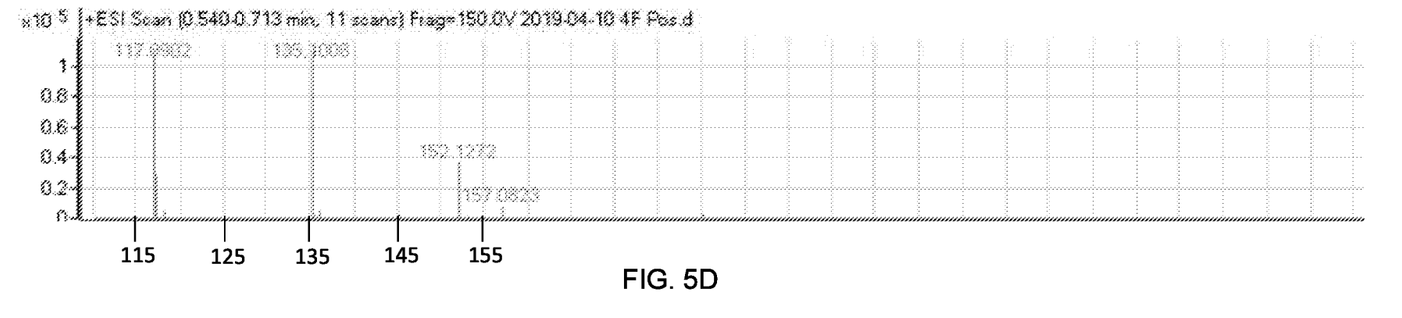
Figure 5E:
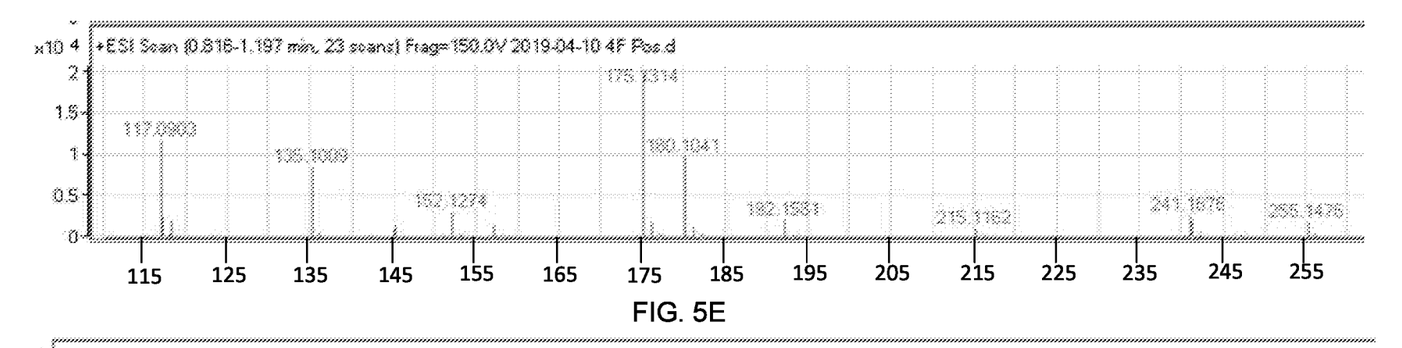
Figure 5F:
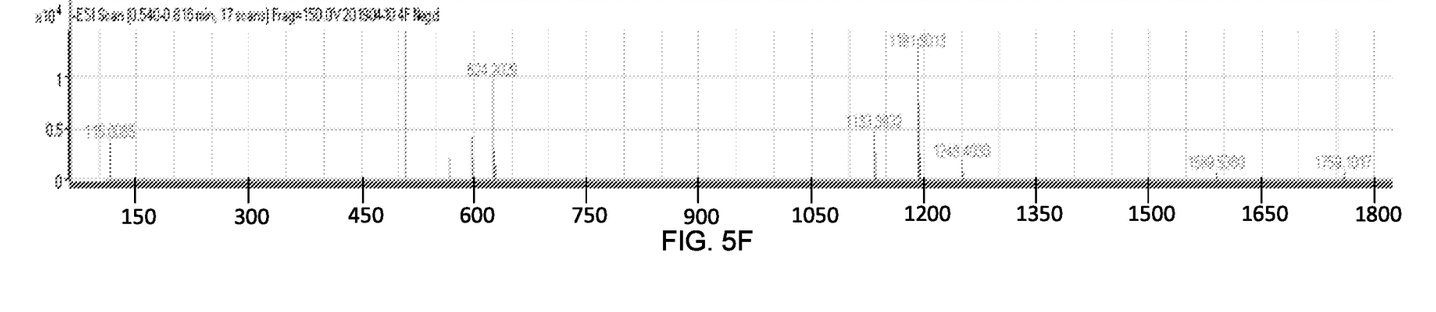
Figure 5G:
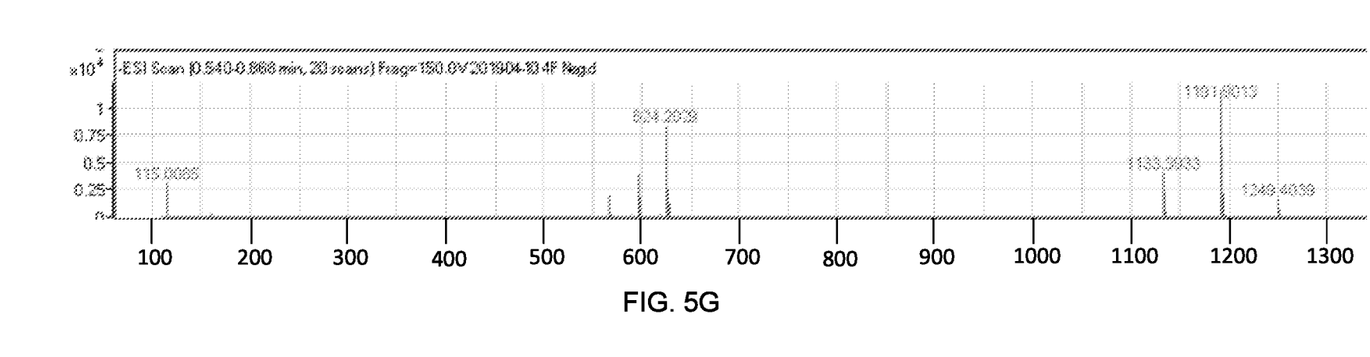
Figure 6A:
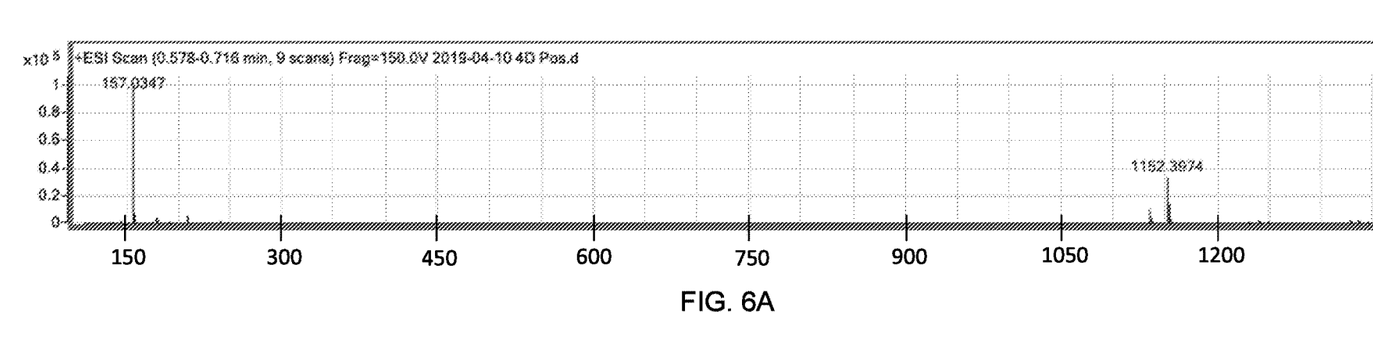
FIGS. 6A-6G show mass spectrometry results for a control solution of TMB in the conventional solvent DMSO.
Figure 6B:
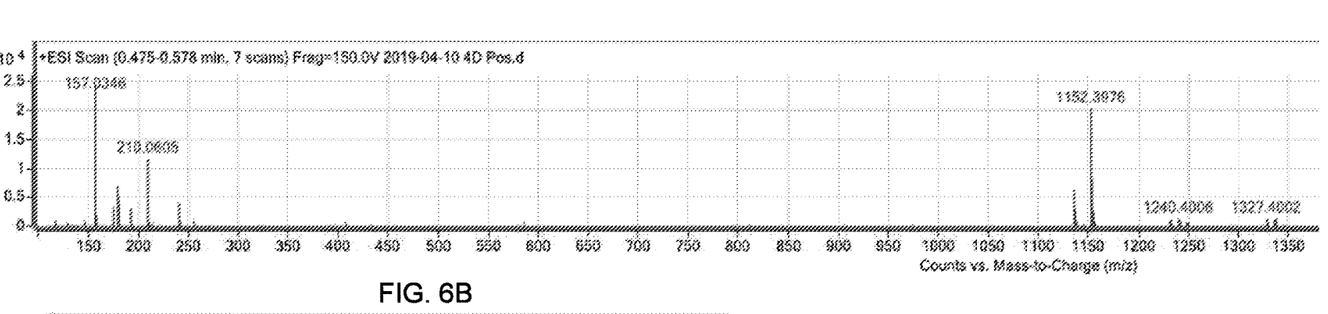
Figure 6C:
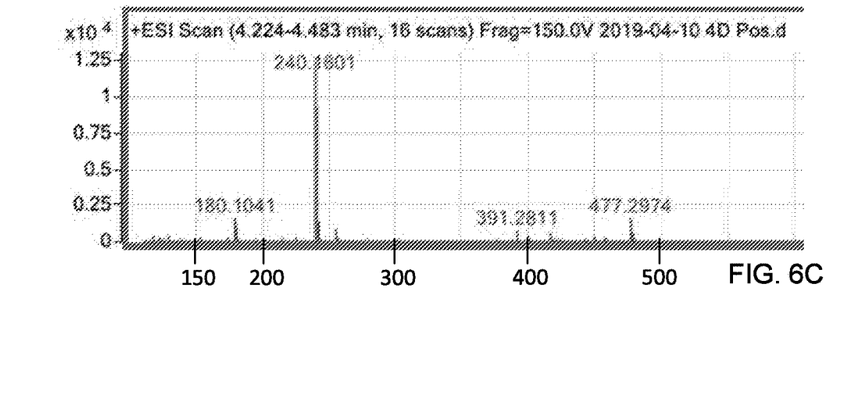
Figure 6D:
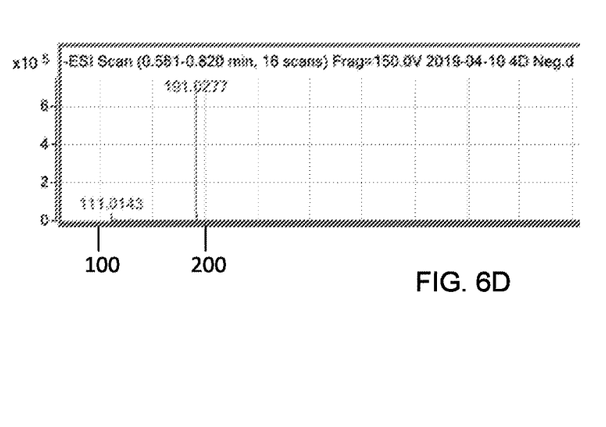
Figure 6E:
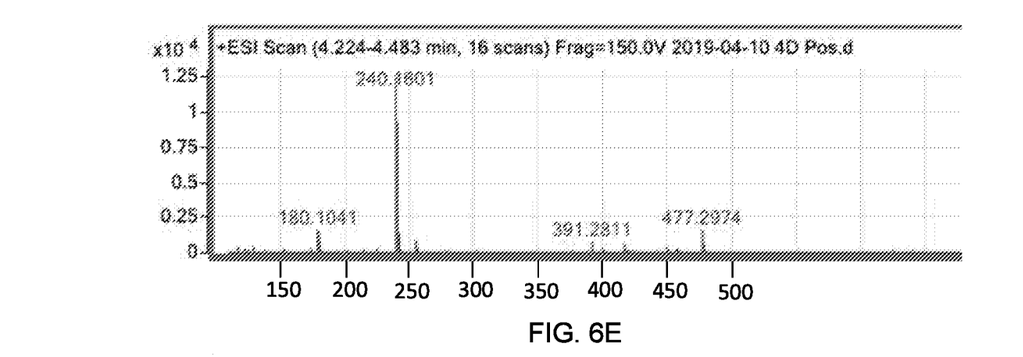
Figure 6F:
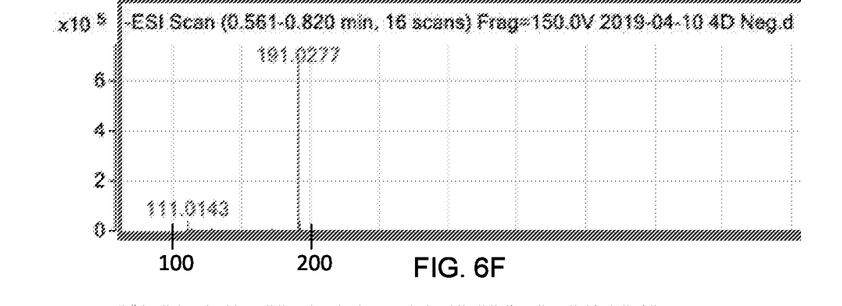
Figure 6G:
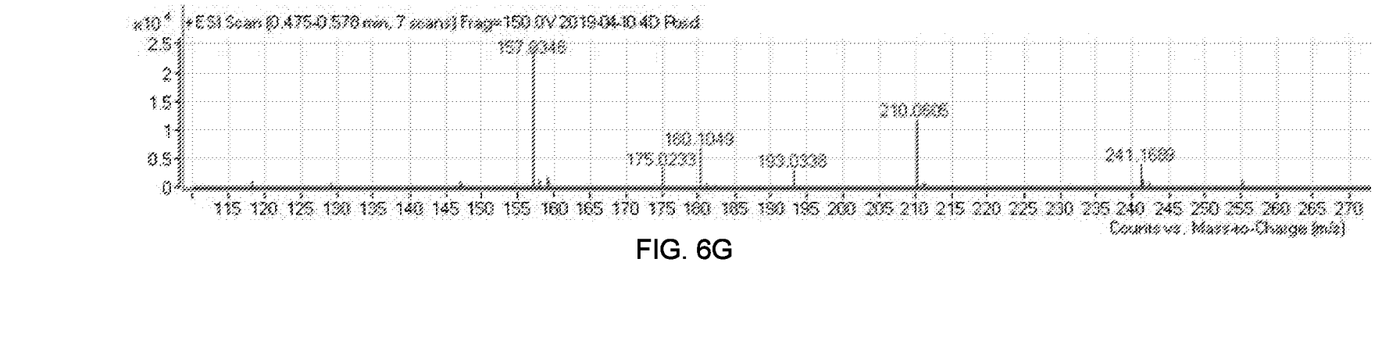

A mass spectrometer (Triple Quadrupole 6495C LC/MS) was used to identify and characterize components of the stable TMB formulations. Results are shown in FIGS. 1A-1G for solution 3C, in FIGS. 2A-2C for solution 3D, in FIGS. 3A-3C for solution 3F, FIGS. 4A-4E for solution 4C, FIGS. 5A-5G for solution 4F, and FIGS. 6A-6G for solution 4D.

Mass spectrometry results for selected molecular weight components observed in the TMB formulations are summarized in Table 2 below.

TABLE 2

Components Contained in Tested TMB Formulations

| | | | | | Control | |
|---|---|---|---|---|---|---|
| | Solution 3C | Solution 4C | Solution 3F | Solution 4F | Solution 3D | Solution 4D |
| 111 | Yes | | | | Yes | Yes |
| 115 | | | Yes | Yes | | |
| 117 | Yes | Yes | Yes | Yes | | |
| 129 | Yes | | | | | |
| 135 | Yes | Yes | Yes | Yes | | |
| 139 | Yes | | | | | |
| 145 | | | Yes | Yes | | |
| 147 | Yes | Yes | | | | |
| 152 | Yes | Yes | Yes | Yes | | |
| 157 | Yes | Yes | Yes | Yes | Yes | Yes |
| 175 | Yes | Yes | | Yes | Yes | Yes |
| 180 | Yes | Yes | Yes | Yes | | Yes |
| 192 | | | | Yes | | |
| 191 | Yes | Yes | Yes | | Yes | Yes |
| 193 | Yes | Yes | | | Yes | Yes |
| 210 | Yes | Yes | Yes | | Yes | Yes |
| 215 | Yes | | | Yes | Yes | |
| 240 | Yes | | | Yes | | Yes |
| 241 | Yes | Yes | | Yes | | Yes |
| 255 | Yes | Yes | | Yes | | Yes |
| 268 | | Yes | | | | |
| 391 | | | | | | Yes |
| 407 | Yes | | | Yes | | |
| 477 | Yes | | | | | Yes |
| 624 | | | | Yes | | |
| 1133 | | | | Yes | | |
| 1152 | Yes | Yes | | Yes | | Yes |
| 1191 | | | | Yes | | |
| 1240 | | Yes | | | | Yes |
| 1249 | | | | Yes | | |
| 1327 | | | | | | Yes |
| 1336 | | Yes | | | | |
| 1589 | | | | | Yes | |
| 1759 | | | | | Yes | |

When DMSO was mixed with fumaric acid (in solution 4D) or citric acid (in solution 3D) and heated, neither solution 3D nor 4D was stable. These solutions had a visibly decreased colour change reaction after one month, and no colour change after two months of storage.

Solutions 3C, 4C, 3F and 4F were observed to be stable. Without being bound by theory, it is believed that propylene glycol dimers and/or trimers are formed when propylene glycol and an acid such as fumaric acid or citric acid are mixed and heated at about 50° C. to 80° C. The propylene glycol dimers and/or trimers stabilize TMB.

Example 3.0—Stability of the TMB Formulations

In one example, a solution of TMB prepared in polyethylene glycol in accordance with Example 1.0 was evaluated for stability. It was determined that the solution was stable at room temperature (i.e. 22° C.) for a period of at least two years. It was further determined that the solution was stable at 37° C. for a period of at least two months.

In another example embodiment, Solution 4F was produced and subjected to mass spectrometry in Example 2.0 above 7 months after the initial preparation of the solution. Testing as described below demonstrated that the resulting solution of TMB is stable.

To determine the stability of the TMB formulations, samples of Solutions 3C, 3D, 3F, 4C, 4D, 4F were withdrawn at predetermined time intervals and analyzed by adding to chlorine solutions having a total chlorine concentration of about 1 ppm. All of samples 3C, 3F, 4C and 4F caused the chlorine solutions to change from colourless to a blue colour over time, including at least after one month and two months of storage, demonstrating that the TMB in the samples was stable. The colour change yielded by control solutions 3D and 4D of TMB in DMSO was markedly reduced after one month of storage, and after two months of storage these solutions did not cause the chlorine solution to change from colourless to a blue colour at all, confirming that TMB was not stable in these formulations.

The inventor has also conducted experiments using the exemplary tetraalkyl benzidine compound N-(3-sulfopropyl)-3,3',5,5'-tetramethylbenzidine and produced stable compositions with this tetraalkyl benzidine compound.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A method for preparing a stable formulation of an alkyl benzidine compound, the method comprising:
   combining a short chain diol having fewer than six carbon atoms and an alkyl benzidine compound to form a solution, the solution having a low pH; and
   heating the solution with moderate heat in the range of 50° C. to 80° C.

2. A method as defined in claim 1, wherein the alkyl benzidine compound is a dialkyl benzidine compound or a tetraalkyl benzidine compound.

3. A method as defined in claim 1, wherein the alkyl benzidine compound has the general formula (I):

wherein $R_1$ and $R_2$ each independently is an alkyl group having from 1 to 6 carbon atoms, $R_3$ and $R_4$ each independently is an alkyl group having 1 to 6 carbon atoms or a hydrogen atom, $R_5$ and $R_6$ each independently is an alkyl group having 1 to 8 carbon atoms or a hydrogen atom, and $R_7$ and $R_8$ each independently is a hydrogen atom, a sulfoalkyl group having 1 to 8 carbon atoms which may have one or more hydroxyl groups, or a carboxyalkyl group having 1 to 8 carbon atoms which may have one or more hydroxyl groups, and $R_7$ and $R_8$ are not simultaneously H.

4. A method as defined in claim 1, wherein the alkyl benzidine compound is N,N'-bis(2-sulfoethyl)-3,3'-dimethylbenzidine; N,N'-bis(3-sulfopropyl)-3,3'-dimethylbenzidine; N,N'-bis(2-hydroxy-2-sulfoethyl)-3,3'-dimethylbenzidine; N,N'-bis(2-hydroxy-3-sulfopropyl)-3,3'-dimethylbenzidine; N,N'-bis(4-sulfobutyl)-3,3'-dimethylbenzidine; N,N'-bis(3-sulfopropyl)-N,N'-diethyl-3,3'-dimethylbenzidine; N,N'-bis(2,4-disulfobenzyl)-3,3'-dimethylbenzidine; N-(2-sulfoethyl)-3,3',5,5'-tetramethylbenzidine; N-(3-sulfopropyl)-3,3',5,5'-tetramethylbenzidine; N-(4-sulfobutyl)-3,3',5,5'-tetramethylbenzidine; N-(2-hydroxy-2-sulfoethyl)-3,3',5,5'-tetramethylbenzidine; N-(2-hydroxy-3-sulfopropyl)-3,3',5,5'-tetramethylbenzidine; N-(2,4-disulfobenzyl)-3,3',5,5'-tetramethylbenzidine; N,N'-bis(2-sulfoethyl)-3,3',5,5'-tetramethylbenzidine; N,N'-bis(3-sulfopropyl)-3,3',5,5'-tetramethylbenzidine; N,N'-bis(4-sulfobutyl)-3,3',5,5'-tetramethylbenzidine; N,N'-bis(2-hydroxy-2-sulfoethyl)-3,3',5,5'-tetramethylbenzidine; N,N'-bis(2-hydroxy-3-sulfopropyl)-3,3',5,5'-tetramethylbenzidine; or N,N'-bis(2,4-disulfobenzyl)-3,3',5,5'-tetramethylbenzidine.

5. A method as defined in claim 1, wherein the alkyl benzidine compound is 3,3',5,5'-tetramethylbenzidine (TMB).

6. A method as defined in claim 1, wherein the short chain diol is propylene glycol.

7. A method as defined in claim 1, wherein the low pH is provided by adding an acid to the solution.

8. A method as defined in claim 1, wherein the low pH is in the range of 2.0 to 6.0.

9. A method as defined in claim 7, wherein the acid comprises an organic acid.

10. A method as defined in claim 9, wherein the organic acid comprises a short chain saturated or unsaturated carboxylic acid having less than 6 carbon atoms.

11. A method as defined in claim 7, wherein the acid comprises fumaric acid ($C_4H_4O_4$), citric acid ($C_6H_8O_7$), malic acid ($C_4H_6O_5$), lactic acid ($C_3H_6O_3$), acetic acid ($C_2H_4O_2$), hydrochloric acid (HCl), sulfuric acid ($H_2SO_4$), carbonic acid ($H_2CO_3$) or phosphoric acid ($H_3PO_4$).

12. A method as defined in claim 1, further comprising: mixing beta-cyclodextrin with the solution, either before or after said heating.

13. A method as defined in claim 1, wherein said heating is conducted for a treatment period of between 10 minutes and 10 hours.

14. A method as defined in claim 1, wherein said heating step results in the formation of dimers, trimers or oligomers of the short chain diol that stabilize the alkyl benzidine compound.

15. A method of detecting total chlorine in an aqueous solution, the method comprising:
preparing a stable formulation of an alkyl benzidine compound by combining a short chain diol having fewer than six carbon atoms and an alkyl benzidine compound to form a solution, the solution having a low pH, and heating the solution with moderate heat in the range of 50° C. to 80° C.;
mixing the resulting stable formulation with the aqueous solution to yield a mixed solution; and
evaluating a visual characteristic of the mixed solution to detect the total chlorine in the aqueous solution.

16. A method as defined in claim 15, wherein the aqueous solution comprises dialysis water.

17. A method of detecting free chlorine in an aqueous solution, the method comprising:
preparing a stable formulation of an alkyl benzidine compound by combining a short chain diol having fewer than six carbon atoms and an alkyl benzidine compound to form a solution, the solution having a low pH, and heating the solution with moderate heat in the range of 50° C. to 80° C.;
mixing the resulting stable formulation with the aqueous solution to yield a mixed solution; and
evaluating a visual characteristic of the mixed solution to detect the free chlorine in the aqueous solution.

18. A stable formulation as defined in claim 1, wherein the short chain diol comprises at least 99% vol./vol. of the stable formulation.

\* \* \* \* \*